(12) United States Patent
Schilling et al.

(10) Patent No.: US 11,497,905 B2
(45) Date of Patent: Nov. 15, 2022

(54) ALGORITHM FOR UTILIZING MULTIPLE INPUTS TO MODULATE THE CHARGING RATE OF A FULLY IMPLANTABLE SYSTEM

(71) Applicant: Medtronic, Inc., Minneapolis, MN (US)

(72) Inventors: Eric A. Schilling, Ham Lake, MN (US); Erin N. Reisfeld, Minneapolis, MN (US); Thomas W. Radtke, Ramsey, MN (US); Brian D. Kuhnley, Delano, MN (US); David Siegfried, Edina, MN (US)

(73) Assignee: Medtronic, Inc., Minneapolis, MN (US)

( * ) Notice: Subject to any disclaimer, the term of this patent is extended or adjusted under 35 U.S.C. 154(b) by 163 days.

(21) Appl. No.: 15/930,491

(22) Filed: May 13, 2020

(65) Prior Publication Data

US 2021/0353838 A1 Nov. 18, 2021

(51) Int. Cl.
*A61M 60/50* (2021.01)
*A61M 60/148* (2021.01)
*H02J 7/00* (2006.01)

(52) U.S. Cl.
CPC .......... *A61M 60/50* (2021.01); *A61M 60/148* (2021.01); *H02J 7/0047* (2013.01); *A61M 2205/3365* (2013.01); *A61M 2205/3368* (2013.01); *A61M 2205/8206* (2013.01)

(58) Field of Classification Search
CPC ..... A61N 1/378; A61N 1/3787; A61M 60/50; A61M 60/871
See application file for complete search history.

(56) References Cited

U.S. PATENT DOCUMENTS

| 4,925,443 A | 5/1990 | Heilman et al. |
|---|---|---|
| 9,192,704 B2 | 11/2015 | Yomtov et al. |
| 10,376,625 B2 | 8/2019 | Bluvshtein et al. |
| 2003/0191504 A1* | 10/2003 | Meadows .......... A61N 1/36071 607/33 |

(Continued)

FOREIGN PATENT DOCUMENTS

| WO | 2010042012 A1 | 4/2010 |
|---|---|---|
| WO | 2015160806 A2 | 10/2015 |

(Continued)

OTHER PUBLICATIONS

International Search Report and Written Opinion dated Mar. 21, 2021, for corresponding International Application No. PCT/US2021/012046; International Filing Date: Jan. 4, 2021 consisting of 11-pages.

*Primary Examiner* — Michael J D'Abreu
(74) *Attorney, Agent, or Firm* — Shumaker & Sieffert, P.A.

(57) ABSTRACT

A controller implantable within the body of a patient as part of a left ventricular assist device (LVAD) system and a method therefore are provided. According to one aspect, the controller includes processing circuitry configured to receive inputs from at least one of: at least one internal component of the LVAD system, at least one external component of the LVAD system, and at least one clinician's device, and determine a charging rate for charging a battery of the LVAD system internal to the patient based on at least one of the received inputs.

20 Claims, 8 Drawing Sheets

(56) References Cited

U.S. PATENT DOCUMENTS

| | | | |
|---|---|---|---|
| 2009/0112291 A1* | 4/2009 | Wahlstrand | A61N 1/3787 607/61 |
| 2012/0154143 A1 | 6/2012 | Ambrosio | |
| 2012/0157755 A1* | 6/2012 | D'Ambrosio | A61M 60/148 600/16 |

FOREIGN PATENT DOCUMENTS

| | | |
|---|---|---|
| WO | 2017021846 A1 | 2/2017 |
| WO | 2017025606 A1 | 2/2017 |

* cited by examiner

ALGORITHM FOR UTILIZING MULTIPLE INPUTS TO MODULATE THE CHARGING RATE OF A FULLY IMPLANTABLE SYSTEM

CROSS-REFERENCE TO RELATED APPLICATION n/a

FIELD

The present technology is generally related to implantable devices such as a left ventricular assist device (LVAD), and more particularly to utilization of multiple inputs to modulate a charging rate of an implantable system.

BACKGROUND

Referring to FIG. 1, an implantable LVAD system 10 has internal components (in the body of the patient) and external components. The LVAD system 10 may typically include an LVAD pump 12 an implanted controller (i-controller) 14 having an internal battery 16, an implanted internal transcutaneous energy transfer system (TETS) coil (i-coil) 18, an external TETS coil (e-coil) 20 and an external power transmitter 22 with a detachable battery 24. In operation, power is supplied from the external power transmitter 22 to the i-controller 14 via mutual coupling of the coils 18 and 20, in order to charge i-controller 14 and to power the LVAD pump 12. The coils 18 and 20 transfer power by mutual induction of electromagnetic energy over the air and through the body. The power supplied by the external power transmitter 22 may come from the detachable battery 24 or from a wall outlet, for example.

SUMMARY

The techniques of this disclosure generally relate to utilization of multiple inputs to modulate and set a charging rate of an implantable system such as an LVAD system. According to one aspect, an algorithm (computer instructions) collects, coordinates and communicates inputs from both internal and external components to allow the internal controller to establish a charging rate. Automating charging rate decisions based on a plurality of inputs may reduce (and possibly even minimize) the need for human interaction. Automating charging rate decisions may provide significant hazard mitigation, resulting in an improved safety/efficacy profile of the system. Automating charging rate decisions may also improve patient acceptance of the system.

In one aspect, the present disclosure provides a controller implantable within the body of a patient as part of a left ventricular assist device (LVAD) system. The controller includes processing circuitry configured to receive inputs from at least one of: at least one internal component of the LVAD system, at least one external component of the LVAD system, and at least one clinician's device. The processing circuitry is further configured to determine a charging rate for charging a battery of the LVAD system internal to the patient based on at least one of the received inputs.

According to this aspect, in some embodiments, an input from the at least one internal component includes at least one of a speed and a temperature of an LVAD pump of the LVAD system. In some embodiments, an input from the at least one internal component includes at least one of a temperature and a capacity of the battery. In some embodiments, an input from the at least one internal component includes a temperature of the controller. In some embodiments, an input from the at least one external component includes a transmitter case temperature. In some embodiments, an input from the at least one external component includes a temperature of a surface of at least one transcutaneous energy transfer system (TETS) component. In some embodiments, the processing circuitry is further configured to notify the patient of a high temperature of at least one of an internal component and an external component of the LVAD system. In some embodiments, the processing circuitry is further configured to notify the patient of at least one option to reduce temperature of the at least one of the internal component and the external component of the LVAD system.

According to another aspect, a method implemented in a controller implantable within the body of a patient as part of a left ventricular assist device (LVAD) system is provided. The method includes receiving inputs from at least one of: at least one internal component of the LVAD system, at least one external component of the LVAD system, and at least one clinician's device. The method also includes determining a charging rate for charging a battery of the LVAD system internal to the patient based on at least one of the received inputs.

According to this aspect, in some embodiments, an input from the at least one internal component includes at least one of a speed and a temperature of an LVAD pump of the LVAD system. In some embodiments, an input from the at least one internal component includes at least one of a temperature and a capacity of the battery. In some embodiments, an input from the at least one internal component includes a temperature of the controller. In some embodiments, an input from the at least one external component includes a transmitter case temperature. In some embodiments, an input from the at least one external component includes a temperature of a surface of at least one transcutaneous energy transfer system (TETS) component. In some embodiments, the patient is notified of a high temperature of at least one of an internal component and an external component of the LVAD system. In some embodiments, the patient is notified of at least one option to reduce temperature of the at least one of the internal component and the external component of the LVAD system.

According to yet another aspect, a LVAD system includes an LVAD pump and an internal controller in electrical communication with the LVAD pump. The internal controller includes processing circuitry configured to receive inputs from at least one of: at least one internal component of the LVAD system, at least one external component of the LVAD system, and at least one clinician's device. The processing circuitry is also configured to determine a charging rate for charging a battery of the LVAD system internal to the patient based on at least one of the received inputs.

According to this aspect, in some embodiments, the determination of a charging rate is based at least in part on internal temperature measurements. In some embodiments, the determination of a charging rate is based at least in part whether a battery storage level is above a threshold level. In some embodiments, the determination of a charging rate includes selecting among a group of predefined rates.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1:
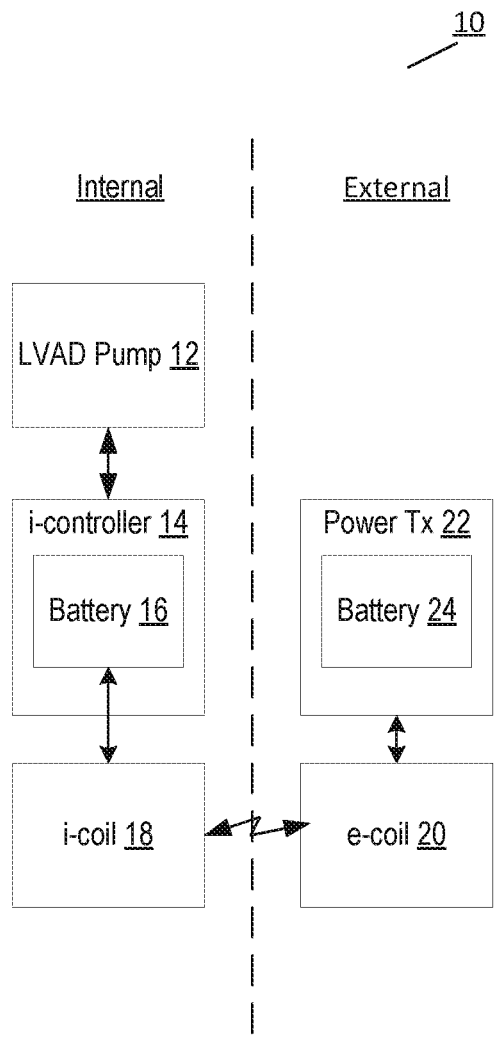
FIG. 1 is a block diagram of an implantable LVAD system.
Figure 2:
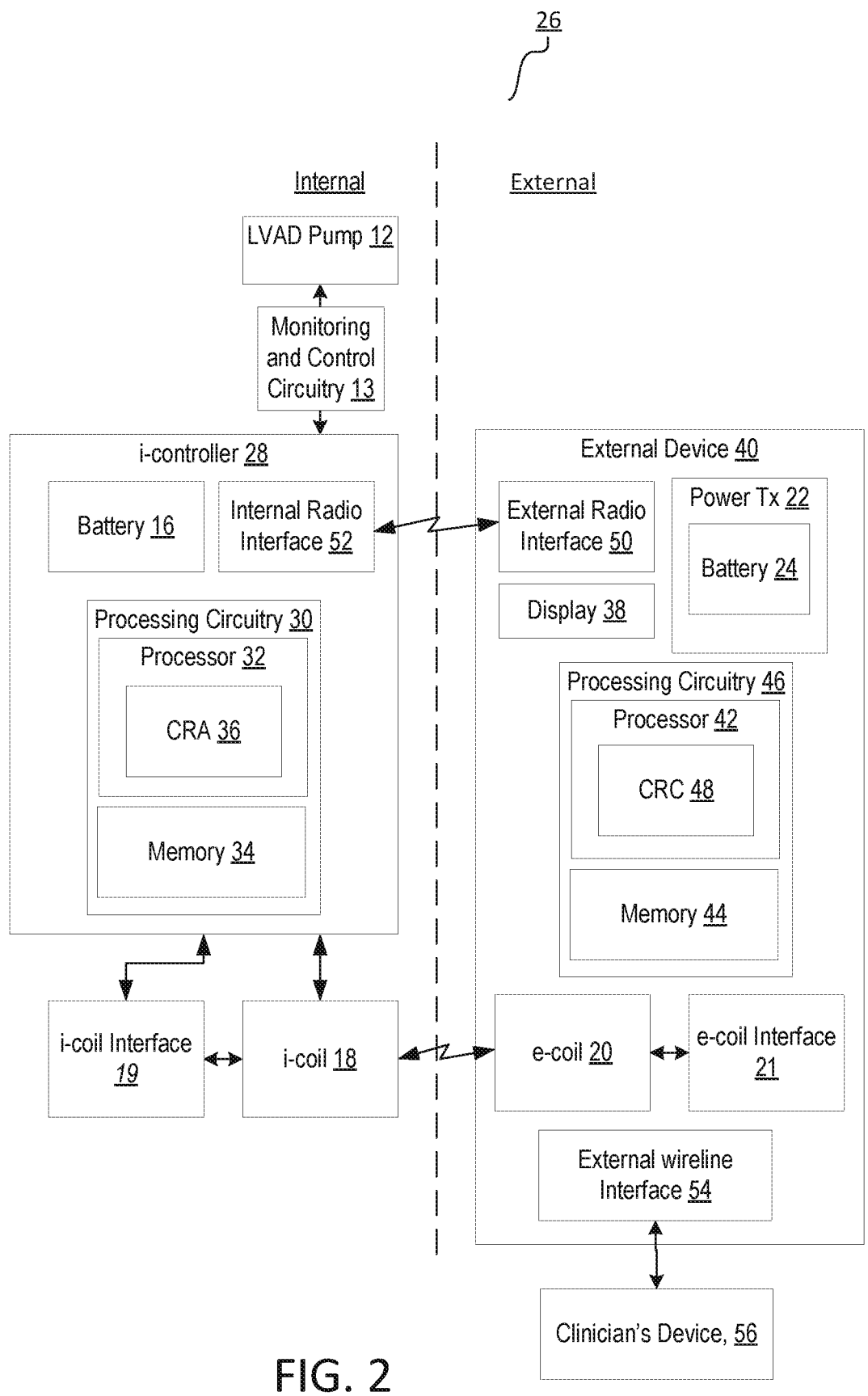
FIG. 2 is a block diagram of an embodiment of an LVAD system that implements a charging rate algorithm according to principles disclosed herein.

Some embodiments described herein are related to utilization of multiple inputs to modulate and/or set a charging rate of an LVAD system. FIG. 2 shows a block diagram of one example configuration of an LVAD system 26 having an internal component such as an internal controller (i-controller) 28 configured to perform functions including selection and modulation or adjustment of charging rates based on inputs from internal and external components of the LVAD system. The i-controller 28 may have processing circuitry 30 which may include a processor 32 and a memory 34. The processor 32 may be configured to execute computer instructions stored in the memory 34. Those instructions may include instructions to cause the processor to perform the algorithms described in more detail below. The processor 32 may therefore implement a charging rate algorithm (CRA) 36, which is described in detail below with reference to FIGS. 4-7.

A variable charging rate and message(s) produced by the charging rate algorithm 36 may be transferred from the i-controller 28 to an external display 38 of an external device 40, which may include a processor 42 and a memory 44 within processing circuitry 46, the external power transmitter 22 and the detachable battery 24, as well as the e-coil 20 in some embodiments. The memory 44 may be configured to store computer instructions to be executed by the processor 42 and may also be configured to store the value of the charging rate and other charging rate-related information, including a message indicating the reason for the selected charging rate. The processor 42 may implement a charging rate controller (CRC) 48 to receive charging rate-related information and control a rate of transfer of power of the external power transmitter 22. The external display 38 may be configured to display charging rate-related information received from the charging rate algorithm 36.

Electrical communication of signals and power between the internal components of i-controller 28 may be via communication busses and individual electrical conductors not shown in FIG. 2. For example, a multi-conductor address bus and data bus may connect processor 32 with memory 34. In some embodiments, an i-coil interface 19 associated with i-coil 18 may be included in the set of internal components making up the LVAD system 26. One purpose of i-coil interface 19 may be to modulate the alternating current applied to the i-coil 18 with signals from the i-controller 28 to be transmitted from the i-coil 18 to the e-coil 20 and/or to demodulate signals to be received by the i-coil 18 from the e-coil 20. In some embodiments, a purpose of the i-coil interface 19 is to provide conversion between the alternating current (AC) of the i-coil 18 and direct current (DC) to charge the battery 16. The power supplied to the i-coil 18 is adjusted by varying the AC electrical current in the e-coil 20. Some or all functions of the i-coil interface 19 may be included in the i-controller 28 and/or the i-coil 18. Similarly, electrical communication of signals and power between the internal components of external device may be by communication busses and individual electrical conductors not shown in FIG. 2. For example, a multi-conductor address bus and data bus may connect processor 42 with memory 44. In some embodiments, an e-coil interface 21 associated with e-coil 20 may be included in the set of internal components making up the LVAD system 26. One purpose of e-coil interface 21 may be to modulate the alternating current applied to the e-coil 20 with signals from the processing circuitry 46 to be transmitted from the e-coil 20 to the i-coil 18 and/or to demodulate signals received by the e-coil 20 from the i-coil 18.

In some embodiments, the internal components of the LVAD system 26 may include monitoring and control circuitry 13. A purpose of monitoring and control circuitry 13 may include monitoring speed and temperature, for example, of the LVAD pump 12. Another purpose of the monitoring and control circuitry 13 may include controlling the speed of the LVAD pump 12. In some embodiments, some or all of the monitoring and control circuitry 13 may be incorporated into the LVAD pump 12 and/or the i-controller 28. In some embodiments, some or all of the functions performed by the monitoring and control circuitry 13 may be performed by the processing circuitry 30. Thus, in some embodiments, the monitoring and control circuitry 13 may include one or more temperature sensors embedded in the LVAD pump 12. Information obtained from and/or about the LVAD pump 12, such as speed and temperature, may be sent to the external device 40 to be displayed by external display 38. The speed and temperature of the LVAD pump 12 may also be input to the charging rate algorithm (CRA) 36.

The various internal components making up the LVAD system may be grouped into one or more separate housings. Similarly, the various external components making up the LVAD system may be grouped into one or more separate housings. Further, some of the components shown and described as being internal to the i-controller 28 may be instead, external to i-controller 28 in some embodiments. Similarly, some of the components shown and described as being internal to the external device 40 may be instead, external to external device 40 in some embodiments. Note further, the some of the functions performed by processor 32, such as some or all of the functions of charging rate algorithm 36, may be performed instead by processor 42. For example, all of the inputs to the charging rate algorithm 36 originating from internal components of the LVAD system 26 may be transmitted to the external device wirelessly and the processor 42 could use these inputs to determine a charging rate, in some embodiments. Subsequently, the determined charging rate could be used by the charging rate controller 48 to control the rate at which the external power transmitter 22 transmits power to the LVAD pump 12 and/or battery 16 via the TETS coils 18 and 20.

The selected charging rate may be one that is calculated and/or selected from a group of predetermined charging rates. For example, in some embodiments, there may be three charging rates: slow, medium and fast. In some embodiments, fast charging provides on the order of 1 to 1 charge, where the discharge rate for a nominal pump power is roughly matched by a charge rate of the internal battery. In some embodiments a medium charging rate may depend on or be based on temperature measurements or estimates, and may further be based on patient comfort. In some embodiments, a slow charging rate may be a rate sufficient to ensure charging progress even with occasional coil misalignment. (Coil misalignment reduces power transfer from the external power transmitter 22 to the internal battery 16, and also may cause an increase in temperature of internal and external components.) In some embodiments, the medium charging rate may be the initial charging rate or a default charging rate. In some embodiments, different charging rates can be programmed by the clinician or the patient. These computer instructions for programming different charging rates may be transferred from the external device 40 to the memory 34 either prior to implantation or after implantation.

The transfer of the computer instructions from the external source to the internal memory 34 may be by electrical conductor or by wireless radio frequency (RF) transmission prior to implantation, and may be by wireless RF transmission (over the air and through the body) after implantation of the LVAD. Similarly, the transmission of the selected charging rate and related message(s) may be performed wirelessly. Accordingly, in some embodiments, the external device 40 includes an external radio interface 50 and the i-controller 28 includes an internal radio interface 52. In some embodiments, the external radio interface 50 and the internal radio interface 52 are RF transceivers having both an RF receiver for receiving information wirelessly and an RF transmitter for transmitting information wirelessly. Such RF transceivers may be Bluetooth and/or Wi-Fi compliant, for example.

Note that a charging rate selected by the charging rate algorithm 36 may be based on one or more various conditions and/or events. Such conditions and events may include high internal and/or external temperatures, presence of a foreign object in the vicinity of the internal coil 18, insufficient power headroom, reserve capacity, LVAD pump speed. Insufficient power headroom refers to a measure of the margin between power available (via the battery and/or via the coils) and the power required to maintain pump speed. Reserve capacity refers to a threshold of capacity remaining in the internal battery nearing the end of its ability to provide power. For example, the charging rate may change from a clinician-programmed charging rate to a slow charging rate in the event that there is insufficient power headroom and internal battery capacity remaining is more than the reserve capacity and the speed of the LVAD pump 12 is at a minimum set speed. As another example, the charging rate may change from the slow charging rate to the clinician-programmed rate in the event that there is sufficient power headroom, or the internal battery capacity is less than the reserve capacity and the LVAD pump speed is at a programmed set speed. Once the charging rate is determined, it may be sent to the external device 40 to be used by the charging rate controller 48 to control the rate at which the external power transmitter 22 transmits power to the LVAD pump 12 and/or battery 16 via the TETS coils 18 and 20. Note that the battery 16 may include a bank of power storage to store reserve power for the LVAD pump 12. The battery 16 may also include a separate bank of power storage to store reserve power for other internal components of the LVAD system 26.

The external device 40 could be a patient's external device that has an external wireline interface 54 which provides an interface between the external device 40 and a clinician's device 56. The clinician's device 56 might, for example, have a USB port and wireline interface 54 might include a USB port, so that a USB cable may connect the two ports. The clinician's device 56 may read data from the external device 40 and write information and control signaling to the external device 40, in some embodiments. Note that the interface to the clinician's device 56 could also be a wireless interface, such as a Bluetooth® interface.

Figure 3:
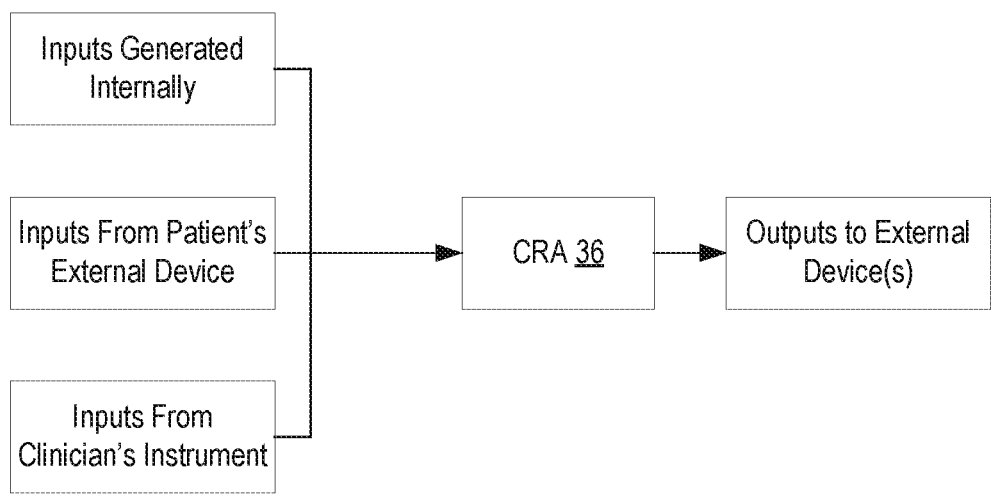
FIG. 3 illustrates inputs to a charging rate algorithm.

FIG. 3 shows a chart of inputs from various sources to the charging rate algorithm (CRA) 36 that may be implemented by the i-controller 28. One source of inputs may be those generated by internal components of the LVAD system 26. Note that receiving an input from a temperature sensor or other sensor in proximity to an internal component is referred to herein as receiving an input from the internal component. These inputs may include one or more of temperature and/or capacity of the battery 16, temperature of the i-coil 18, temperature of a surface of the i-controller 28 or internal region of the i-controller 28, time of day, LVAD pump speed and/or LVAD pump temperature. Another source of inputs may be those generated by components of a patient's external device such as external device 40. Note that receiving an input from a temperature sensor or other sensor in proximity to an external component is referred to herein as receiving an input from the external component. These inputs may include one or more of a patient preferred charging rate, temperature of the external power transmitter 22, temperature of the external battery 24 and/or temperature of the external TETS coil e-coil 20. Temperatures are detected by appropriately placed temperature sensors. In come embodiments, inputs may be received from a clinician's device 56. One such input could be a clinician's preferred charging rate. Another such input could be computer code to be stored in memory 44, and/or memory 34, to program or reprogram the processor 42 and/or the processor 32. All of these inputs to the charging rate algorithm (CRA) 36 may be processed according to steps described below to produce at least a charging rate and a message indicating the applied charging rate selected by the charging rate algorithm 36 and optionally, a message indicating why a particular charging rate was selected.

Figure 4:
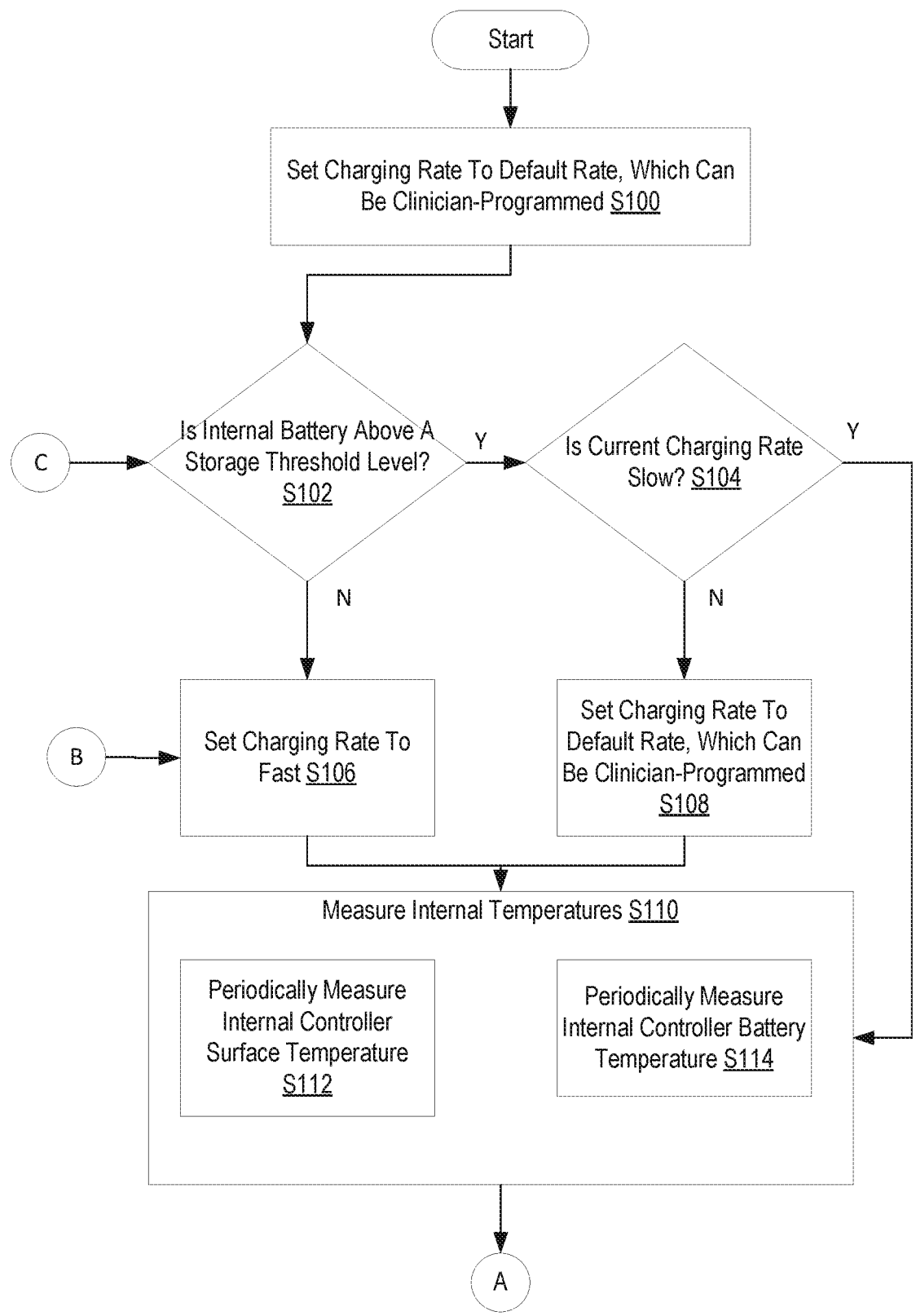
FIG. 4 is a flowchart of a first part of process of determining and setting a charging rate including measuring internal temperatures and internal battery supply.

FIG. 4 is a flowchart of a first part of an example algorithm for selecting charging rates. The blocks shown in FIG. 4 may be performed in whole or in part by internal components of the LVAD system 26. In Block S100, a charging rate is set to a default rate. This default rate may be programmed by the clinician's device 56, for example. In decision Block S102, a determination is made via the CRA 36 whether storage of the internal battery 16 is above a threshold level. If so, a further determination is made whether the current charging rate is slow (Block S104), where as noted above, in some embodiments, there may be slow, medium and fast charging rates to select from. If the current charging rate is slow (Block S104), then internal temperatures are periodically measured (Block S110). If the current charging rate is not slow (Block S104), then the charging rate is set to the default rate (Block S108). Returning to Block S102, if the storage of the internal battery is below the threshold level, the CRA 36 sets the charging rate to fast (Block S106). This may be done with special dispatch in some embodiments. At Block S110, internal temperatures are measured. These may include periodic measurement of i-controller 28 surface temperature (Block S112) (top and/or bottom surfaces, for example) and/or periodic measurement of battery 16 temperature (Block S114). Periodic measurements might occur every 1 minute, for example. The periodicity of measurements may be programmable. Example thresholds in a running mode may include an i-controller top surface threshold of 43 degrees Celsius (C), bottom surface threshold of 41 degrees C., a CEM43 calculation threshold of 20 minutes, and a battery temperature threshold of 54 degrees C. In some embodiments, higher i-controller thresholds are selected in a pre-implant mode. (CEM43 is a known thermal dose standard used throughout the industry and stands for cumulative equivalence minutes at 43 C).

Figure 5:
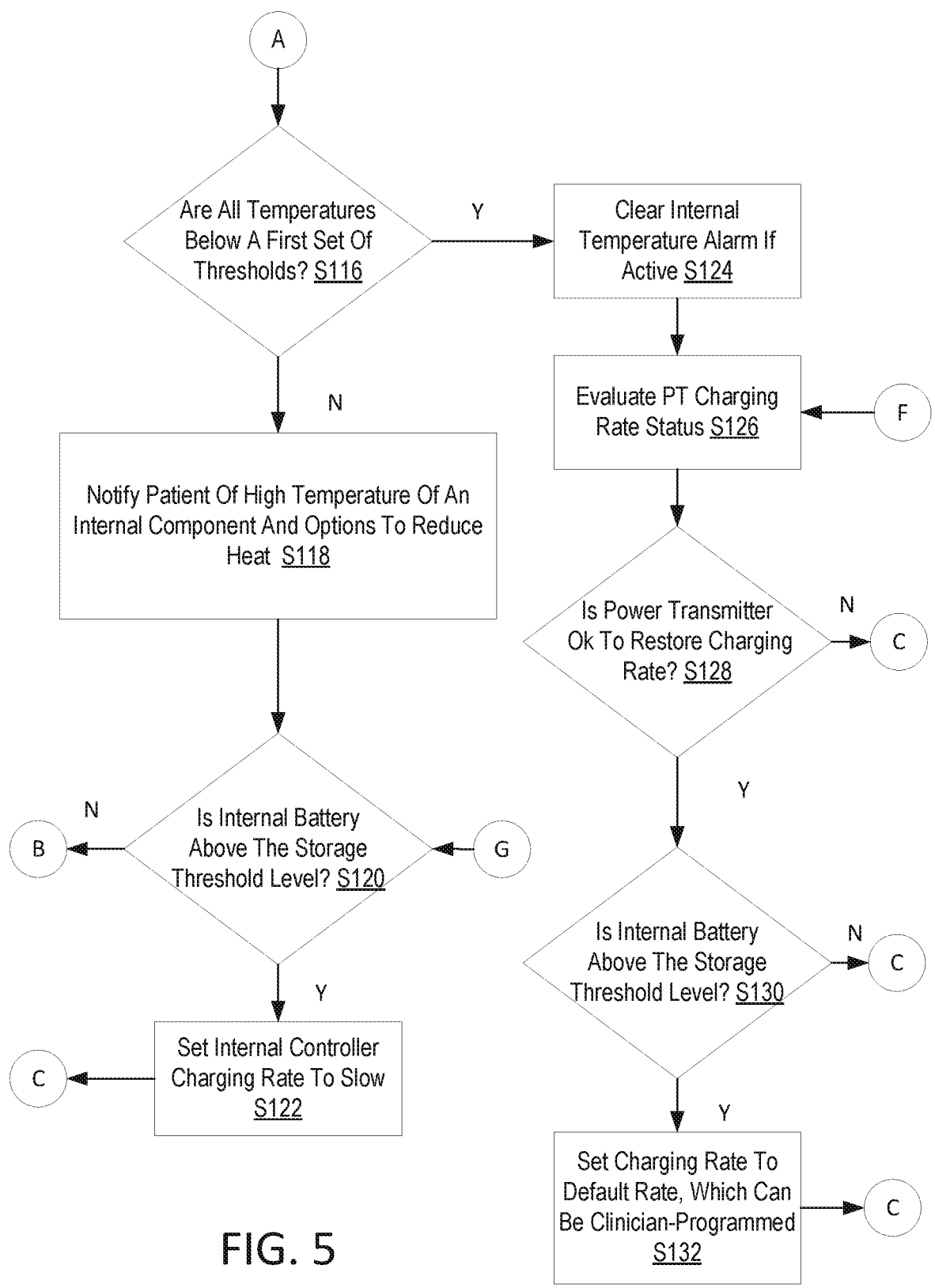
FIG. 5 is a flowchart of a second part of the process of determining and setting a charging rate including notifying the patient of internal heat conditions.

Progress continues along path A, shown in FIG. 5, in this example. The blocks shown in FIG. 5 may be performed in whole or in part by internal components of the LVAD system 26. In FIG. 5, a determination is made as to whether all temperatures are below a first set of respective thresholds (Block S116). If all temperatures are not below the first set of respective thresholds, then the patient is notified of a high temperature condition of an internal component of the LVAD system 26, and is further notified of options to reduce heat (Block S118). The options to reduce heat may include applying a change in an alignment of the TETS coils 18 and 20, change environments (for example, by removing insulation, moving to shade or air conditioning), apply ice packs and calling a clinician. If all temperatures are below the first set of respective thresholds (Block S116), the process continues at Block S124. Otherwise, after notification (Block S118), determination is made if storage of the internal battery is above its respective threshold level (Block S120). If not, the progress flows to Block S106 of FIG. 4. Otherwise, the charging rate determined by the i-controller 28 is set to slow (Block S122). Returning to Block S116, if all temperatures are below the first set of respective thresholds, then an internal temperature alarm, which may be stored in a register of the memory 34, is cleared if set (Block S124). The external power transmitter 22 charging rate status is evaluated (Block S126). A determination is made by the CRA 36 whether the external transmitter may restore a previous charging rate (Block S128). If not, the progress flows to Block S102 of FIG. 4. If the transmitter may restore a previous charging rate (Block S128), then a determination is made whether storage of the internal battery 16 is above a threshold level (Block S130). Storage of the internal battery refers to a level of battery storage indicating an amount of reserve capacity available to the LVAD pump, and optionally also indicating an amount of reserve capacity available to other internal components of the LVAD system 26. If the storage of the internal battery 16 is not above the threshold level, the progress flows to Block S102 of FIG. 4. One reason for this is that from a safety mitigation perspective, quickly charging the battery to above the threshold is prioritized, regardless of component temperatures. This help mitigate the potential for pump stoppage due to insufficient power if there is occasional misalignment of the coils. If the storage of the internal battery 16 is above the threshold level (Block S130), the charging rate may be set to the default charging rate (medium, for example) (Block S132). Note that in this case, as in other cases, the default rate may be programmed by the clinician via the clinician's device 56.

Figure 6:
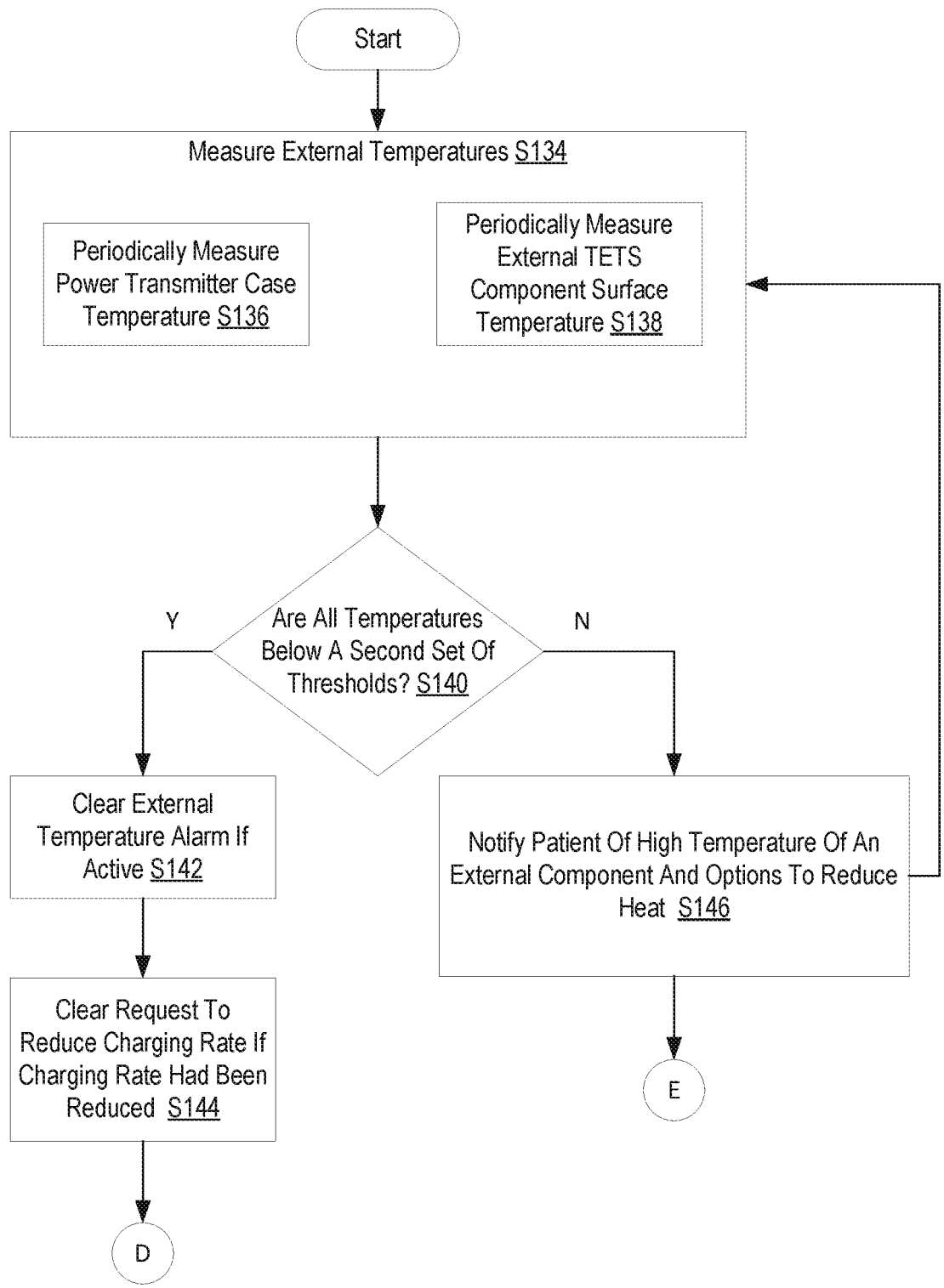
FIG. 6 is a flowchart of a third part of the process of determining and setting a charging rate including measuring external temperatures.

FIG. 6 is a first part of a flowchart of one example process for providing inputs and/or controlling the CRA 36. The blocks shown in FIG. 6 may be performed in whole or in part by external components of the LVAD system 26, possibly including the clinician's device 56. In Block S134, external temperatures S134 are measured. These measurements include periodically measuring the temperature of the case of the external power transmitter 22 (Block S136) and/or periodically measuring the surface temperature of the external TETS and e-coil 20 (Block S138). A determination is made whether all external temperatures are below a second set of respective thresholds (Block S140). If so, an external alarm, which may be stored in memory 44, is cleared if set (Block S142). A request to reduce the charging rate is cleared by the CRA 16 if the charging rate had been reduced (Block S144). The progress then flows to path D of FIG. 7. Returning to Block S140, if not all temperatures are below the second set of respective thresholds, then the patient is notified of high temperature of an external component of the LVAD system 26 and is further notified of options to reduce heat (Block S146). These options may include one or more of connecting the external device 40 to AC power (from a wall outlet, for example), realign TETS coils 18 and 20, move the external radio interface 50 closer to the internal radio interface 52, change the environment, change external power transmitter 22, and/or call a clinician. The progress then flows to path E of FIG. 7.

Figure 7:
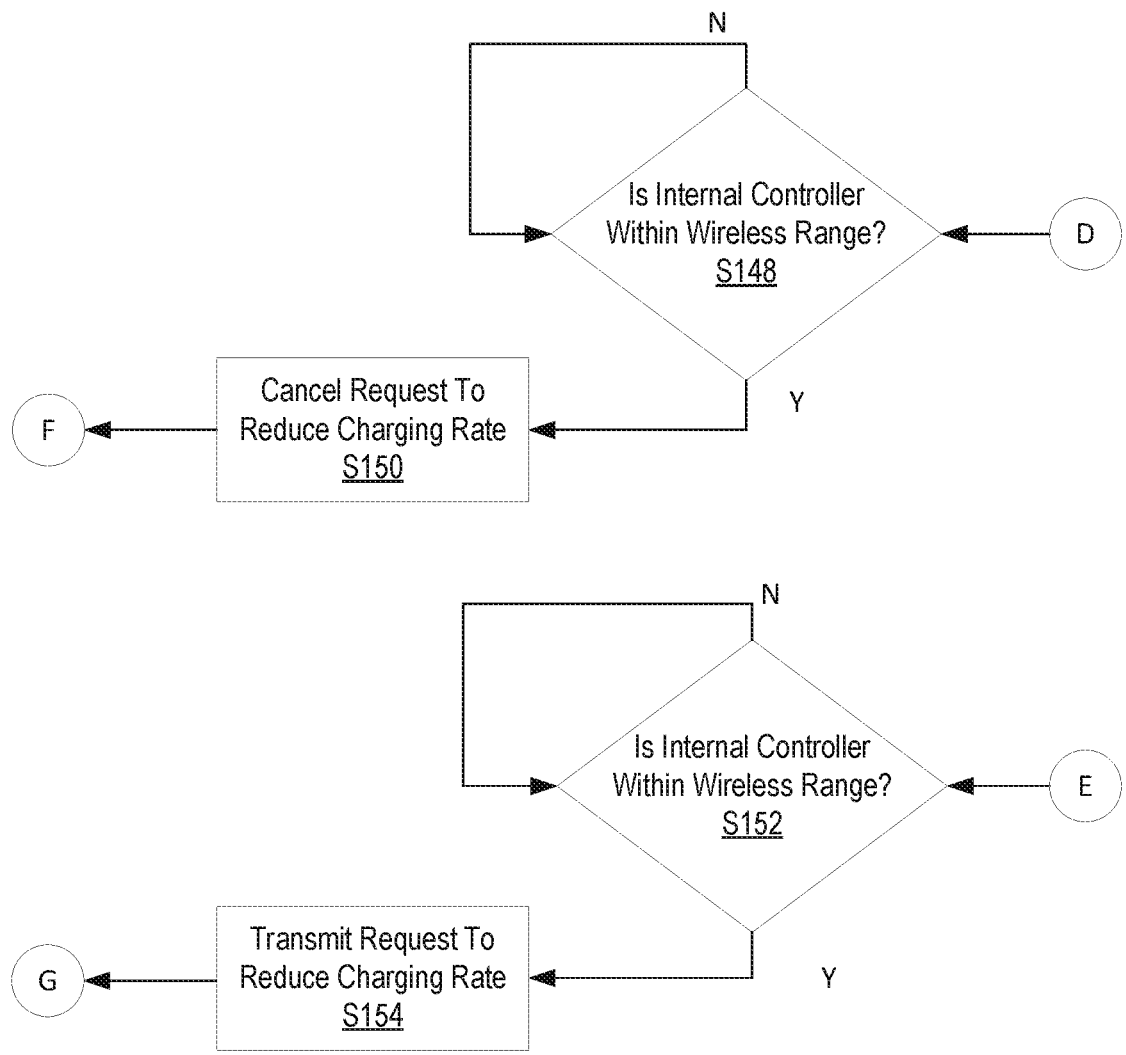
FIG. 7 is a flowchart of a fourth part of the process of determining and setting a charging rate including determining if an internal controller is within wireless range of an external RF interface.

In FIG. 7, the blocks may be performed in whole or in part by external components of the LVAD system 26, possibly including the clinician's device 56. Along path D, in Block S148, whether the i-controller 28 is within wireless range of the external device 40 (i.e., whether the two radio interfaces 50 and 52 are within range to receive signals from each other wirelessly) may be determined by the processor 42 and/or the external radio interface 50. If the two devices are within wireless range, the external power transmitter 22 and/or the processor 42 and/or the external radio interface 50 may cause cancellation of a request to reduce the charging rate (Block S150), and progress then flows to Block S126 of FIG. 5. Along path E, in Block S152, whether the i-controller 28 is within wireless range of the external device 40 may be determined by the processor 42 and/or external radio interface 50. If the two devices are within wireless range, the external power transmitter 22 and/or the processor 42 and/or the external radio interface 50 may send to the i-controller 28 a request to reduce the charging rate (Block S154). Progress then flows to Block S120 of FIG. 5.

Figure 8:
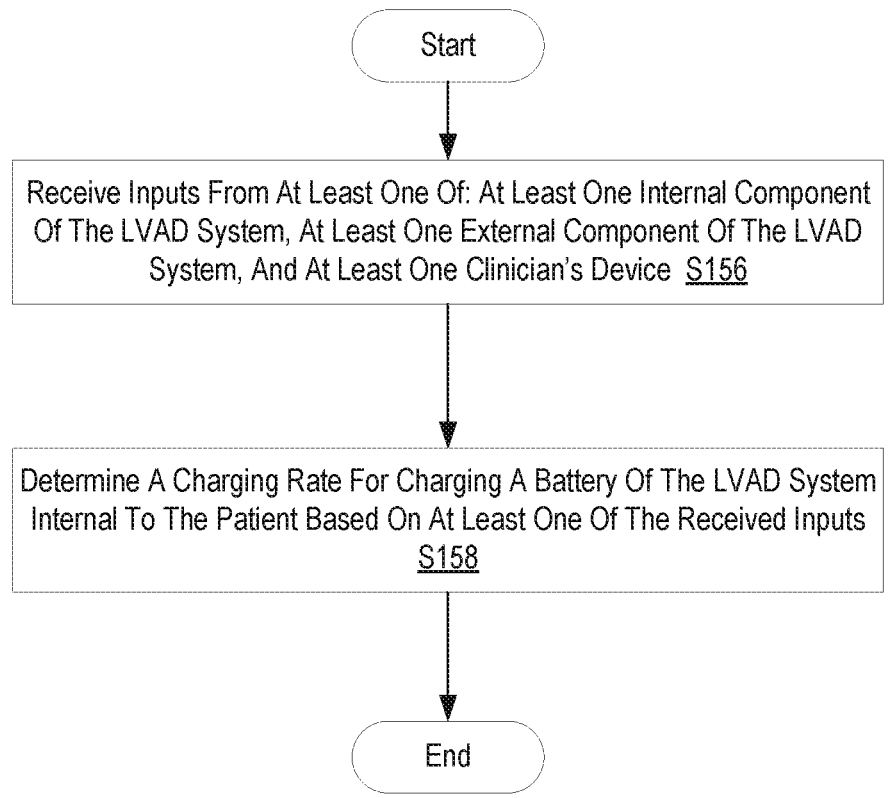
FIG. 8 is a flowchart of a process for determining a charging rate based on a plurality of inputs.

FIG. 8 is a flowchart of a process for determining a charging rate based on a plurality of inputs. The process includes receiving inputs from at least one of: at least one internal component of the LVAD system, at least one external component of the LVAD system, and at least one clinician's device (Block S156). The process also includes determining a charging rate for charging a battery of the LVAD system internal to the patient based on at least one of the received inputs (Block S158).

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media and memory may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A controller implantable within the body of a patient as part of a left ventricular assist device (LVAD) system, the controller including processing circuitry configured to:
   receive inputs from at least one of: at least one internal component of the LVAD system, at least one external component of the LVAD system, and at least one clinician's device, wherein the inputs include at least a charge level of a battery of the LVAD system and a speed of an LVAD pump of the LVAD system; and
   determine a charging rate for charging a battery of the LVAD system internal to the patient based on at least the charge level of the battery of the LVAD system and the speed of the LVAD pump.

2. The controller of claim 1, wherein the processing circuitry is further configured to determine the charging rate for charging the battery of the LVAD system internal to the patient based on at least the charge level of the battery of the LVAD system and the speed of the LVAD pump by:
   determining whether the charge level of the battery of the LVAD system satisfies a critical condition;
   determining whether the speed of the LVAD pump of the LVAD system satisfies a minimum speed condition;
   responsive to determining that the charge level of the battery satisfies the critical condition and determining that the speed of the LVAD pump satisfies the minimum speed condition, causing the battery of the LVAD system to charge at a first charging rate; and
   responsive to determining that the charge level of the battery satisfies the critical condition and determining that the speed of the LVAD pump satisfies the minimum speed condition, causing the battery of the LVAD system to charge at a second charging rate, wherein the first charging rate is smaller than the second charging rate.

3. The controller of claim 2, wherein the processing circuitry is configured to determine that the charge level of the battery satisfies the critical condition when a power headroom of the battery is equal to or less than a power headroom threshold value.

4. The controller of claim 2, wherein the processing circuitry is configured to determine that the charge level of the battery satisfies the critical condition when an internal capacity of the battery is equal to or greater than a reserve capacity threshold value.

5. The controller of claim 2, wherein the processing circuitry is configured to determine that the speed of the LVAD pump satisfies the minimum speed condition when the speed of the LVAD pump is equal to or less than a minimum speed threshold value.

6. The controller of claim 1, wherein the processing circuitry is further configured to:
   determine whether one or more temperature inputs satisfies a temperature condition; and
   responsive to determining that the one or more temperature inputs satisfies the temperature condition, generate a notification that indicates that the LVAD system is operating at a high temperature.

7. The controller of claim 6, wherein the one or more temperature inputs comprise:
   temperature inputs from internal components comprising:
      a temperature of the battery and a temperature of the controller; and
   temperature inputs from external components comprising:
      a transmitter case temperature and a temperature of a surface of at least one transcutaneous energy transfer system (TETS) component.

8. The controller of claim 7, wherein the processing circuitry is configured to determine that the one or more temperature inputs satisfies the temperature condition when at least one of the one or more temperature inputs is equal to or greater than a corresponding temperature threshold value.

9. The controller of claim 1, wherein the processing circuitry is further configured to:
   determine a time of day;
   responsive to determining that the time of day is a first time, cause the battery of the LVAD system to charge at the second charging rate; and
   responsive to determining that the time of day is a second time, cause the battery of the LVAD system to charge at the first charging rate, wherein the first time is earlier in the day than the second time.

10. The controller of claim 9, wherein the processing circuitry is further configured to:
    receive a patient preferred charging rate and a clinician preferred charging rate;
    responsive to determining that the time of day is a first time, cause the battery of the LVAD system to charge at the second charging rate; and
    responsive to determining that the charge level of the battery does not satisfy the critical condition and determining that the speed of the LVAD pump does not satisfy the minimum speed condition, cause the battery of the LVAD system to charge at a rate based on at least one of the patient preferred charging rate or the clinician preferred charging rate.

11. A left ventricular assist device (LVAD) system, comprising:
    an LVAD pump; and
    an internal controller in electrical communication with the LVAD pump, the internal controller including processing circuitry configured to:

receive inputs from at least one of: at least one internal component of the LVAD system, at least one external component of the LVAD system, and at least one clinician's device, wherein the inputs include at least a charge level of a battery of the LVAD system and a speed of an LVAD pump of the LVAD system; and determine a charging rate for charging a battery of the LVAD system internal to the patient based on at least the charge level of the battery of the LVAD system and the speed of the LVAD pump.

12. The LVAD system of claim 11, wherein the processing circuitry is further configured to determine the charging rate for charging the battery of the LVAD system internal to the patient based on at least the charge level of the battery of the LVAD system and the speed of the LVAD pump by:

determining whether the charge level of the battery of the LVAD system satisfies a critical condition;

determining whether the speed of the LVAD pump of the LVAD system satisfies a minimum speed condition;

responsive to determining that the charge level of the battery satisfies the critical condition and determining that the speed of the LVAD pump satisfies the minimum speed condition, causing the battery of the LVAD system to charge at a first charging rate; and responsive to determining that the charge level of the battery satisfies the critical condition and determining that the speed of the LVAD pump satisfies the minimum speed condition, causing the battery of the LVAD system to charge at a second charging rate, wherein the first charging rate is smaller than the second charging rate.

13. The LVAD system of claim 12, wherein the processing circuitry is configured to determine that the charge level of the battery satisfies the critical condition when a power headroom of the battery is equal to or less than a power headroom threshold value.

14. The LVAD system of claim 12, wherein the processing circuitry is configured to determine that the charge level of the battery satisfies the critical condition when an internal capacity of the battery is equal to or greater than a reserve capacity threshold value.

15. The LVAD system of claim 12, wherein the processing circuitry is configured to determine that the speed of the LVAD pump satisfies the minimum speed condition when the speed of the LVAD pump is equal to or less than a minimum speed threshold value.

16. The LVAD system of claim 11, wherein the determination of the charging rate is further based at least in part on internal temperature measurements.

17. The LVAD system of claim 11, wherein to determine the charging rate is further based at least in part whether a battery storage level is above a threshold level.

18. The LVAD system of claim 11, wherein to determine the charging rate, the internal controller is further configured to select among a group of predefined rates.

19. A method implemented in a controller implantable within the body of a patient as part of a left ventricular assist device (LVAD) system, the method including:

receiving inputs from at least one of: at least one internal component of the LVAD system, at least one external component of the LVAD system, and at least one clinician's device wherein the inputs include at least a charge level of a battery of the LVAD system and a speed of an LVAD pump of the LVAD system; and determining a charging rate for charging a battery of the LVAD system internal to the patient based on at least the charge level of the battery of the LVAD system and the speed of the LVAD pump.

20. The method of claim 19, wherein determining the charging rate for charging the battery of the LVAD system internal to the patient based on at least the charge level of the battery of the LVAD system and the speed of the LVAD pump comprises:

determining whether the charge level of the battery of the LVAD system satisfies a critical condition;

determining whether the speed of the LVAD pump of the LVAD system satisfies a minimum speed condition;

responsive to determining that the charge level of the battery satisfies the critical condition and determining that the speed of the LVAD pump satisfies the minimum speed condition, causing the battery of the LVAD system to charge at a first charging rate; and responsive to determining that the charge level of the battery satisfies the critical condition and determining that the speed of the LVAD pump satisfies the minimum speed condition, causing the battery of the LVAD system to charge at a second charging rate, wherein the first charging rate is smaller than the second charging rate.

* * * * *